(12) United States Patent
Berezin et al.

(10) Patent No.: US 9,945,056 B2
(45) Date of Patent: Apr. 17, 2018

(54) BINDER FOR FLUSHABLE NON-WOVEN FABRIC

(71) Applicant: ALBAAD MASSUOT YITZHAK, LTD., M.P. Sde Gat (IL)

(72) Inventors: Oleg Berezin, Maale Adumim (IL); Asaf Izraely, Rishon LeZion (IL); Dan Rizkov, Beitar Illit (IL); Moshe Voskoboinik, Maale Adumim (IL); Boris Gorelik, Zur Hadassa (IL)

(73) Assignee: Albaad Massuot Yitzhak Ltd., M.P. Sde Gat (IL)

( * ) Notice: Subject to any disclaimer, the term of this patent is extended or adjusted under 35 U.S.C. 154(b) by 215 days.

(21) Appl. No.: 14/415,864

(22) PCT Filed: Jul. 20, 2014

(86) PCT No.: PCT/IL2014/050655
§ 371 (c)(1),
(2) Date: Jan. 20, 2015

(87) PCT Pub. No.: WO2015/011701
PCT Pub. Date: Jan. 29, 2015

(65) Prior Publication Data
US 2016/0040338 A1 Feb. 11, 2016

(30) Foreign Application Priority Data

Jul. 22, 2013 (IL) .......................................... 227606

(51) Int. Cl.
| | | |
|---|---|---|
| *D04H 1/587* | (2012.01) | |
| *A61F 5/44* | (2006.01) | |
| *D04H 1/64* | (2012.01) | |
| *A61F 13/15* | (2006.01) | |
| *A61L 15/62* | (2006.01) | |
| *C08F 220/06* | (2006.01) | |
| *B65B 5/04* | (2006.01) | |
| *B65B 61/00* | (2006.01) | |
| *C08F 222/10* | (2006.01) | |
| *C08L 33/06* | (2006.01) | |

(52) U.S. Cl.
CPC ............... *D04H 1/587* (2013.01); *A61F 5/44* (2013.01); *A61F 13/15211* (2013.01); *A61L 15/62* (2013.01); *B65B 5/04* (2013.01); *B65B 61/00* (2013.01); *C08F 220/06* (2013.01); *C08F 222/10* (2013.01); *C08L 33/06* (2013.01); *D04H 1/64* (2013.01)

(58) Field of Classification Search
USPC ............. 442/149, 150, 154, 327; 15/104.93; 524/560
See application file for complete search history.

(56) References Cited

U.S. PATENT DOCUMENTS

| | | | |
|---|---|---|---|
| 3,689,314 A | 9/1972 | Duchane | |
| 3,692,725 A | 9/1972 | Duchane | |
| 3,805,165 A | 4/1974 | Hoffman | |
| 4,528,344 A * | 7/1985 | Chang | .................... C08G 12/42 |
| | | | 525/509 |
| 5,312,883 A | 5/1994 | Komatsu et al. | |
| 5,317,063 A | 5/1994 | Komatsu | |
| 5,384,189 A | 1/1995 | Kuroda | |
| 5,509,913 A | 4/1996 | Yeo | |
| 6,423,804 B1 | 7/2002 | Chang | |
| 6,429,261 B1 | 8/2002 | Lang | |
| 7,276,459 B1 | 10/2007 | Lang et al. | |
| 2013/0189198 A1* | 7/2013 | Tamareselvy | ........ A61K 8/8152 |
| | | | 424/49 |

FOREIGN PATENT DOCUMENTS

| | | |
|---|---|---|
| CN | 101735412 | 6/2010 |
| EP | 0 469 429 A2 | 7/1991 |
| EP | 0 608 460 | 8/1994 |
| JP | 6233809 | 8/1994 |
| WO | 98/53006 | 11/1998 |
| WO | 9853006 A1 | 11/1998 |
| WO | 1999/06456 | 2/1999 |
| WO | 1999/18269 | 4/1999 |
| WO | 2001/68157 | 9/2001 |
| WO | 01/83666 A2 | 11/2001 |
| WO | 0183666 A2 | 11/2001 |
| WO | 02/077048 | 10/2002 |
| WO | 02077048 A2 | 10/2002 |

OTHER PUBLICATIONS

Database WPI Week 201051 Thomson Scientific London GB AN2010 J06559 & CN 101735412 A (Univ Shaanxi Sci & Tech. Jun. 16, 2010).
Supplemental European Search Report for a counterpart foreign application, 6 pages, dated Jan. 7, 2015.
International Search Report from a foreign patent office in a counterpart foreign application, dated Oct. 6, 2014.
Written opinion from a foreign patent office in a counterpart foreign application, dated Sep. 23, 2014.

* cited by examiner

*Primary Examiner* — Lynda Salvatore
(74) *Attorney, Agent, or Firm* — Roach Brown McCarthy & Gruber, P.C.; Kevin D. McCarthy

(57) ABSTRACT

The invention provides ion-sensitive, hard water-dispersible quaterpolymers as binders for making flushable nonwoven fabrics which are compatible with house and municipal drain-lines.

13 Claims, No Drawings

BINDER FOR FLUSHABLE NON-WOVEN FABRIC

FIELD OF THE INVENTION

The invention relates to ion-sensitive, hard water-dispersible polymers and to their use as binder compositions in the creation of disposable and flushable, nonwoven fabrics. The disposable nonwoven fabrics have sufficient strength to be used as pre-moistened wipes while also being capable of disintegrating in such a way that they are compatible with buildings and municipal drain-lines, conveyance and waste treatment systems. The polymer binder of the invention is a copolymer derived from four distinct monomers which are: acrylic acid, butyl acrylate, 2-ethylhexyl acrylate, and an allyl derivative of polyethylene-glycol (PEG), such as diethylene glycol monoallyl ether.

BACKGROUND OF THE INVENTION

The production of disposable fabrics, including wet wipes, disposable diapers, incontinent garments, and feminine care products, is constantly studied. However, one of the major problems is to create an economical coherent fibrous web, which will easily dissolve or disintegrate in water, while still maintaining in-use strength. Without such an in-use strength, such a product could not be easily used and pulled from its package, and without its dissolvability properties, it would not be possible or advisable to dispose of it by simply flushing it down the toilet.

Disposable fabrics can be used in various ways, such as disposable wipes, and can be incorporated in other products, such as diapers, feminine care products, and adult incontinent care products. Said fabrics are typically formed by wet or dry (air) laying a generally random plurality of fibers and joining them together to form a coherent web with a binder. However, known binders tend not to degrade, thus preventing or diminishing the degradation of the disposable product. Several laying technologies are known in the art, for example, wet-laying, air-laying, or carding. Bonding technologies are also known in the art, e.g. latex bonding, thermo-bonding fibers, or hydro-entanglement by water jets. Often, the nonwoven fabric is carded and bonded by hydro-entanglement, a technology known as Spunlace.

Accordingly, there is a need for binder compositions with improved hard water solubility. Several polymers are known to exhibit cloud points or inverse solubility properties in aqueous media, e.g. as wound dressings with good absorbing characteristics and easy removal (JP 6233809), and as materials in flushable personal care products (U.S. Pat. No. 5,509,913).

Other known binders are ion-sensitive binders. For example, U.S. Pat. No. 5,312,883, U.S. Pat. No. 5,317,063, U.S. Pat. No. 5,384,189 and EP 608460, disclose ion-sensitive polymers based on acrylic acid and alkyl acrylates. However, these binders are not soluble in water containing more than 15 ppm calcium and/or magnesium ions. Notably, U.S. Pat. No. 5,312,883 discloses terpolymers as suitable binders for flushable nonwoven webs.

U.S. Pat. No. 6,423,804 and U.S. Pat. No. 6,429,261 describe the incorporation of sulfonic groups (soft base) into the polymer chain together with carboxylic groups (hard base). These binders are insoluble in a solution containing 2-5% sodium chloride.

Although various ion and temperature sensitive compositions for flushable materials are known, there still exists a need for flushable products having tap water-disintegration in soft and hard water areas, and at the same time having improved strength for better processability and use properties. The binder, to be practically useful, is needed at a reasonable cost without compromising product safety and environmental concerns, something that past and present products fail to do. Moreover, there is a need for flushable products possessing softness, resiliency, and fiber dispersion after toilet flushing so that fibers do not become entangled with obstacles in municipal drain-lines, conveyance and waste treatment systems.

Accordingly, it is an object of the present invention to provide a flushable nonwoven fabric, which comprises an ion-sensitive binder polymer composition that overcomes the drawbacks of the prior art.

It is also an object of the present invention to provide an ion-sensitive binder polymer composition which is insoluble in a salt solution containing about 2 to 5 weight % monovalent or multivalent ions, and which is soluble in tap water containing more than 15 ppm calcium and/or magnesium ions.

It is another object of the invention to use said binder polymer compositions in the manufacture of flushable, nonwoven fabrics. Furthermore, said fabrics can be used to prepare various articles.

The above and other objects and advantages of invention will become apparent as the description proceeds.

SUMMARY OF THE INVENTION

The present invention relates to an ion-sensitive polymer formed from the following monomers: acrylic acid, butyl acrylate, 2-ethylhexyl acrylate, and an allyl derivative of polyethylene-glycol (PEG).

In one embodiment, said allyl derivative PEG is selected from the group consisting of diethylene glycol allyl, triethylene glycol allyl, and tetraethylene glycol allyl, or any combination thereof.

According to one embodiment, the ion-sensitive polymer of the invention is insoluble in a salt solution containing 2-5% monovalent or multivalent ions, and is soluble in tap water 10-300 ppm calcium ions.

The ion-sensitive polymer of the invention comprises from about 30 to about 65 weight % acrylic acid; from about 20 to about 45 weight % butyl acrylate; from about 7 to about 30 weight % 2-ethylhexyl acrylate; and from about 2 to about 20 weight % an allyl derivative of PEG. In a specific embodiment, the ion-sensitive polymer of the invention comprises from about 35 to about 55 weight % acrylic acid; from about 25 to about 40 weight % butyl acrylate; from about 10 to about 25 weight % 2-ethylhexyl acrylate; and from about 5 to about 20 weight % an allyl derivative of PEG.

The present invention further provides a binder composition for binding fibrous material into an integral web, comprising the ion-sensitive polymer of the invention. In one embodiment, the content of ion-sensitive polymer is from about 5% to about 50% by weight, for example from about 10% to about 40% by weight.

The present invention also relates to a disposable and flushable, water-decomposable article comprising a fibrous web and the binder composition of the invention. Said disposable and flushable, water-decomposable article may for example be selected from the group consisting of wet wipes, infant care products, child care products, adult care products, feminine care products, medical care products, surgical products, packaging materials, and household wipes. In a specific embodiment, the substrate of said disposable and flushable, water-decomposable article is a nonwoven fabric.

In a specific embodiment, the content of the binder in the fabric of the invention is no more than 30% by weight relative to the total weight of the fabric. In a more specific embodiment, the content of the binder in the fabric is no more than about 10% by weight relative to the total weight of the fabric, e.g. no more than 2 by weight.

The present invention further relates to a method of producing the disposable and flushable, water-disintegratable article of the invention, comprising the steps of
applying the binder composition as described herein onto the fabric;
drying the fabric;
cutting the fabric into a desired size and shape;
impregnating it with a wet wipe lotion (including wetting composition or wetting solution or wetting agent or suitable liquid);
packing the fabric in a liquid-proof package.

According to one specific embodiment, the binder composition of the invention is applied directly onto the fibers, during or after the formation of the fabric.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In addition, the materials, methods, and examples are illustrative only and are not intended to be necessarily limiting.

DETAILED DESCRIPTION OF THE INVENTION

The polymer of the present invention is formed from only acrylic acid, butyl acrylate, 2-ethylhexyl acrylate, and allyl derivative of polyethylene-glycol (PEG), such as diethylene glycol monoallyl ether.

This polymer contains both hydrophilic (carboxylic, diethylene glycol) and hydrophobic (butyl, 2-ethyl hexyl) groups. The presence of such groups provides good adhesion of the polymer to different substrates, specifically nonwoven fabrics made from different fibers, such as cellulosic fibers (pulp, viscose, Tencel and others), and different synthetic fibers, such as polyester, polypropylene, etc. Said polymer also contains carboxylic groups which provide ion sensitive properties, i.e. solubility which is dependent on the ionic strength of the aqueous solution.

An exemplary polymer according to the invention is a quaterpolymer made of these four monomers: (i) acrylic acid, (ii) butyl acrylate, (iii) 2-Ethyl hexyl acrylate, and (iv) diethylene glycol allyl, referred to hereinafter as ISP 2. ISP 2 has ion-sensitive properties and is insoluble in solution with high ionic strength. For instance, when adding 1-2 drops of a 5% sodium chloride solution into 5 ml of ISP 2 solution (1%), a white cloud of precipitate of ISP 2 is formed. The examination of the molecular weight and glass transition temperature ($T_g$) of an ISP 2 sample showed, for example, about 20 KDa and about 6.5° C., respectively.

Ion-sensitive material suitable for use in disposable and flushable personal care products should, ideally, maintain use-strength under controlled conditions and dissolve or disperse rapidly in soft or hard water such as found in toilets and sinks around the world. It should also be safe (i.e. non-toxic), and economical. The ion-sensitive polymers of the present invention meet the above criterions.

Unlike polymers known in the art, the ion-sensitive polymers of the present invention are soluble even in water containing up to 300 ppm calcium. The polymers of the present invention have been formulated to minimize the known strong interaction between the polymer's anions and the water's cations.

The polymers of the present invention are formed from four monomers such that the resulting polymer has a "hydrophobic/hydrophilic balance", which results in desired trigger properties in soft or hard water. As used herein, the term "soft water" refers to water having a divalent ion content of less than about 15 ppm salt ions; and the term "hard water" refers to water having a divalent ion content of more than about 15 ppm salt ions. By controlling the hydrophobic/hydrophilic balance and the composition of the polymer, ion-sensitive polymers having desired in-use binding strength and water-dispersibility in hard water, are produced.

The polymer binders of the present invention comprise the following four distinct monomers: acrylic acid, butyl acrylate, 2-ethylhexyl acrylate, and an allyl derivative of polyethylene-glycol (PEG). Examples of allyl derivative of PEG suitable for use in the polymer binders of the invention include, but are not limited to, diethylene glycol monoallyl ether, triethylene glycol monoallyl ether, and tetraethylene glycol monoallyl ether.

PEG and PEG derivatives are well known in the art and are broadly used, e.g. as (i) plasticizers (U.S. Pat. No. 3,689,314 and U.S. Pat. No. 3,692,725), (ii) as additives to the polymer blend for decreasing melt viscosity (WO 99/06456), and (iii) for polylactide and polyolefines grafting to provide compatibility with water sensitive polymers (WO 99/06456, WO 01/68157, and WO 99/18269).

The amount of the various monomers used to produce the ion-sensitive polymers of the invention may vary depending on the desired properties of the resulting polymer and the final product. The weight percent of the acrylic acid monomer in the ion-sensitive polymer is from about 30% to about 65%, such as between about 30% and about 55%, or between about 35% and about 55%, or between about 30% and about 50%, or between about 40% and 50%, or between about 45% and about 50%. The weight percent of the butyl acrylate monomer in the ion-sensitive polymer is from about 15% to about 45%, such as between about 20% and about 45%, or between about 20% and about 40%, or between about 25% and about 40%, or between about 25% and about 35%, or between about 25% and about 30%. The weight percent of the 2-ethylhexyl acrylate monomer in the ion-sensitive polymer is from about 7% to about 30%, such as between about 10% and 25%, or between about 10% and about 20%, or between about 10% and about 15%. The weight percent of the allyl derivative of PEG monomer in the ion-sensitive polymer is from about 2% to about 20%, such as between about 5% and 20%, or between about 6% and about 18%.

The ion-sensitive polymers of the present invention may be prepared according to any polymerization method. One example is the radical polymerization in solution. Suitable solvents for the polymerization method include, but are not limited to, acetone, mixtures of acetone and water, and ethyl alcohol or its mixture with water. The polymerization temperature may vary depending on the polymerization solvent, monomers, and initiator used. Notably, when a reflux system is used, the temperature used is the boiling temperature of the solvent.

In a further embodiment of the invention, the ion-sensitive polymers are used as a binder material for flushable or non-flushable products. The non-woven fabrics bonded with the ion-sensitive polymers of the invention remain stable and maintain their integrity while dry or in 2-5% of monovalent and/or multivalent ions, but become soluble in water containing low ions concentration (i.e. from about 15 ppm to about 300 ppm calcium ions).

The binder formulations of the present invention may be applied to any fibrous substrate. The binders are particularly suitable for use in water-dispersible products. Suitable fibrous substrates include nonwoven and woven fabrics, preferably nonwoven fabrics. As used herein, the term "nonwoven fabric" refers to a fabric that has a structure of individual fibers or filaments randomly arranged in a web-like fashion. Nonwoven fabrics can be made from a variety of processes including, but not limited to, air-laid processes, wet-laid processes, hydroentangling processes, staple fiber carding and bonding, and solution spinning.

The binder composition of the invention may be applied to the fibrous substrate by any known process. Suitable processes for applying the binder material include, but are not limited to, printing, spraying, impregnating or any other technique. The amount of binder composition may be metered and distributed uniformly within the fibrous substrate. The binder composition may be distributed throughout the entire fibrous substrate or it may be distributed within a multiplicity of small closely spaced areas. According to one embodiment, uniform distribution of the binder composition is desired. For ease of application to the fibrous substrate, the binder may be dissolved in an aqueous solution, e.g. distilled water, deionized water, etc.

Once the binder composition is applied to the fiber, it is dried by any conventional means. Once dry, the fibrous substrate exhibits improved tensile strength compared to the tensile strength of the untreated wet-laid or dry-laid substrates, while still having the ability to rapidly disintegrate when placed in water. For example, as shown in Example 8, the dry tensile strength of the fibrous substrate may be substantially increased; the increase may be by at least 10%, or by at least 25%, or by at least 50%, or by at least 100% as compared to the dry tensile strength of the substrate not containing the binder of the invention.

In another embodiment of the present invention, the amount of the binder composition present in the resultant fibrous substrate ("add-on"), represents only a small portion by weight of the entire substrate. The amount of said "add-on" can vary, e.g., according to the intended final use of the fibrous material. For example, as shown in Example 4, the "add-on" is from about 1% to about 20% wt of the total weight of the substrate, for example up to 1.5%, or up to 3%, or up to 6%, or up to 9%, or up to 12%. Usually, the "add-on" is from about 1.5 to about 9% of the total weight of the substrate.

The fibers forming the fabrics used as the fibrous substrate can be made from a variety of materials including natural fibers, synthetic fibers, and any combination thereof. The choice of fibers depends upon, for example, the intended end use of the finished fabric and fiber cost. For example, suitable fibrous substrates may include, but are not limited to, natural fibers, e.g. cotton, linen, jute, hemp, wool, wood pulp, etc. Alternatively, regenerated cellulosic fibers such as viscose rayon and cuprammonium rayon, modified cellulosic fibers, or synthetic fibers derived from polyesters, polyamides, polyacrylics, etc., alone or in combination with one another, may also be used. Mixtures of one or more of the above fibers may also be used.

In one embodiment of the invention, the fiber length is of importance when producing the fabrics of the invention. The minimum length of the fibers also depends on the method selected for forming the fibrous substrate. For example, where the fibrous substrate is formed by carding, the length of the fiber should usually be at least about 30 mm in order to insure uniformity. Where the fibrous substrate is formed by air-laid or wet-laid processes, the fiber length may desirably be from about 0.2 to 6 mm. Notably, the present invention is not limited by a specific length, or range of lengths, of the fibers used and includes also fibers having a length of greater than 50 mm. Nevertheless, due to the fact that when using large percentage of fibers of a length greater than 15 mm in a flushable fabric, the dispersed fibers tend to form "ropes", which are undesirable and might clog a home drainage, it is typically desired that the fiber length in the fabric of the invention be about 15 mm or less, and usually of a length of about 0.1 mm to about 15 mm so that the fibers disperse easily or detach from one another when in contact with water. The fibers, particularly synthetic fibers, can also be crimped.

In one embodiment, the fabric of the present invention may be incorporated into various products such as wet wipes, sanitary napkins, surgical dressings, tissues, diapers, etc.

The binder compositions of the invention are also useful for binding fibers of air-laid nonwoven fabrics. These air-laid materials are particularly useful for use as a premoistened wipe. One embodiment of the present invention is the production of disposable wet wipes, from the above-described ion-sensitive polymers and different fibrous materials. For wipes, the nonwoven fabric is, optionally, formed from short fibers. The finished wipes may be individually packaged, preferably in a folded manner, in a moisture proof envelope or packaged in containers holding any desired number of sheets in a liquid-tight package with a wetting agent applied to the wipe.

The term "wet wipe" as used herein should be understood to encompass a combination of a substrate as used in the invention and a liquid composition of the present invention, pre-combined for later use. The term "disposable wet wipe" as used herein should be understood to encompass wipe products which are intended to be discarded after use, i.e. it is not intended to be laundered or reused, although it might be recycled.

In one embodiment of the invention, the wet wipes possess an in-use tensile strength in the cross-direction (CD) of at least 2.0 Newton/5 cm. The tensile strength of the same wet wipe after being soaked for one hour in water having a concentration of about 10-300 ppm of calcium ions, is very low, i.e. less than 1 Newton/5 cm, as the fabric structure is completely deteriorated.

Those skilled in the art will readily understand that the binder formulations and fibrous substrates of the present invention may be employed in the preparation of a wide variety of products, including but not limited to, absorbent personal care products designed to be contacted with body fluids. Such products may only comprise a single layer of the fibrous substrate or may comprise a combination of elements. Although the binder formulations and fibrous substrates of the present invention are particularly suited for personal care products, the binder formulations and fibrous substrates may be employed in a wide variety of other consumer products.

The following examples are set forth to further illustrate the present invention. The below examples, however, should not be construed in any way as limiting the present invention in any manner. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

Binder Synthesis

In one embodiment the binder of the invention is prepared by radical polymerization in non-aqueous solution under nitrogen flow. The solvent for the synthetic procedure may be acetone, ethanol, a mixture of ethanol and acetone, a mixture of acetone with a small quantity of water, and others as earlier described.

General Procedure:
  Mixing acrylic acid, butyl acrylate, 2-ethyl hexyl acrylate and an allyl derivate of polyethylene glycol, in a solvent;
  Inserting the mixture into the reactive vessel;
  Heating the mixture, while bubbling a flow of nitrogen through the reactive mixture;
  Adding an initiator into the reactive mixture;
  Waiting for the competence of polymerization, i.e. from about 3 to about 6 hours;
  Cooling the reactive flask to room temperature;
  Adding sodium hydroxide solution for partially neutralizing the carboxylic groups of the polymer;
  Adding distilled water to the reactive mass for decreasing polymer viscosity.

Example 2

ISP 2 Synthesis

ISP 2 is prepared essentially as detailed in Example 1 above, by radical polymerization in non-aqueous solution under nitrogen flow. The solvent for the synthetic procedure may be acetone, ethanol, the mixture of ethanol and acetone, the mixture of acetone with a small quantity of water, etc.

Procedure:
  Mixing acrylic acid (55 g), butyl acrylate (30 g), 2-ethyl hexyl acrylate (15 g) and an allyl derivate of polyethylene glycol (12 g), in a solvent (a mixture of 108 g ethyl alcohol and 38 g water);
  Inserting the mixture into the reactive vessel;
  Heating the mixture to 70° C., under the flow of nitrogen through the reactive mixture, or in an inert atmosphere;
  Adding the initiator 2,2'-azobis(2-amidino-propane)hydrochloride (0.88 g in 5 g of water) into the reactive mixture within one hour;
  Waiting for an additional 4 hours for the completion of polymerization at 70° C. and nitrogen flow;
  Cooling the reactive flask to room temperature;
  Adding 7.65 g of 48% water solution of sodium hydroxide for partially neutralizing the carboxylic groups of polymer;
  Adding 450 g of distilled water to the reactive mass for decreasing polymer viscosity.
  Operating according to the above procedure the concentration of the final polymer solution was about 15 to 17% by weight.

Example 3

Comparative "Lion" Polymer Synthesis

The synthetic procedure is the same as for ISP 2 in Example 2 above. The synthesis is a radical polymerization.

Procedure:
  Mixing acrylic acid (55 g), butyl acrylate (15 g) and 2-ethyl hexyl acrylate (30 g) in a solvent (a mixture of 108 g ethyl alcohol and 38 g water);
  Inserting the mixture into the reactive vessel;
  Heating the mixture to 70° C., while bubbling a flow of nitrogen through the reactive mixture;
  This is done to eliminate the presence of oxygen in the reactive flask.
  Adding the initiator 2,2'-azobis(2-amidino-propane)hydrochloride (0.88 g in 5 g of water) into the reactive mixture within one hour;
  Waiting for an additional 4 hours for the completion of polymerization at 70° C. and nitrogen flow;
  Cooling the reactive flask to room temperature;
  Adding 7.65 g of 48% water solution of sodium hydroxide for partially neutralizing the carboxylic groups of the polymer;
  Adding 450 g of distilled water to the reactive mass for decreasing polymer viscosity.

Tissue Preparation:
Samples were prepared according to the following procedure:
1. Cutting the control fabric into sample size of 14×15 cm (surface 210 $cm^2$);
2. Weighting the initial sample (IS);
3. Placing the sample in a petri dish, and covering it with 7 g of solution containing ISP 2 per 100 $cm^2$;
4. Waiting for 5 min (impregnation);
5. Drying the sample at a temperature of about 100° C. to about 105° C.;
6. Weighting the dry sample (DS);
7. Determining the add-on (A) as the ratio: (A=) DS weight/IS weight;
8. Cutting the dry samples to:
   a) size 5×14 cm for tensile measurements,
   b) size 10×10 cm for testing of the flushable properties;
9. Wetting the samples with the wetting composition at a ratio of 1:2.5 tissue to wetting composition; and
10. Placing the wet samples (WS) in a flexible film (PE/PET laminate) envelope for a predetermined time.

Tensile and Disintegration Testing of the Tissue Preparation:
After preparation, the samples were impregnated with a wetting composition comprising: at least 2% sodium chloride, and optionally preservative, solubilizing agents, skin conditioning agents, perfume, etc.

The tensile properties were measured in the wet condition.

Different water solutions of the Lion polymer were used for the preparation of the tissue with different add-ons (the added-on polymer's solids to the non-woven substrate). The add-ons and the tensile properties (force at peak measured for the weaker cross-direction of the non-woven fabric) are presented in Table 1:

TABLE 1

|   | Add-on Weight, % | Max. Force N/5 cm |
|---|---|---|
| 1 | 0.0 | 4.4 |
| 2 | 1.5 | 4.8 |
| 3 | 2.8 | 6.6 |
| 4 | 4.0 | 7.9 |
| 5 | 4.8 | 10.8 |
| 6 | 6.1 | 11.2 |
| 7 | 8.2 | 13.0 |
| 8 | 10.1 | 16.1 |

Disintegration Results:

Disintegration was measured in tap water (having about 90 ppm calcium ions). All samples were stable in the hard water after 20 hours of stirring. Loss of weight for all samples was less than 1%, and all samples kept their integrity and shape. Accordingly, the material with the Lion polymer is almost stable even after long soaking in hard water, and it is impossible to observe any flushability properties, indicating that its degree of dispersibility is 0.

Example 4

Examples of Various ISP 2 Compositions

The compositions shown in Table 2 were prepared according to the processes of Examples 1 and 2 above:

TABLE 2

| Syn. No. | Acrylic Acid % | Butyl Acrylate % | 2-Ethyl hexyl Acrylate % | Diethylene glycol allyl % | Triethylene glycol allyl % | Tetraethylene glycol allyl % | M.W. Mn Da |
|---|---|---|---|---|---|---|---|
| 1 | 55 | 30 | 15 | 0 | 0 | 0 | |
| 2 | 49.1 | 26.8 | 13.4 | 10.7 | 0 | 0 | 18300 |
| 3 | 50.9 | 27.8 | 13.9 | 7.4 | 0 | 0 | 12900 |
| 4 | 47.4 | 25.9 | 12.9 | 13.8 | 0 | 0 | 14300 |
| 7 | 50.9 | 27.3 | 13.6 | 0 | 9.1 | 0 | 16400 |
| 8 | 45.8 | 25.0 | 12.5 | 0 | 16.7 | 0 | 18400 |
| 9 | 47.8 | 26.1 | 13.0 | 0 | 13 | 0 | 20100 |
| 12 | 48.2 | 26.3 | 13.2 | 0 | 0 | 12.3 | 15800 |
| 13 | 46.6 | 25.4 | 12.7 | 0 | 0 | 15.3 | |
| 14 | 45.5 | 24.8 | 12.5 | 0 | 0 | 17.4 | |

TABLE 3

| WP No | Added binder solids % | Wet CD strength N/5 cm | Wet CD Elongation (mm) | % disintegration after flask test** |
|---|---|---|---|---|
| Reference* | 0 | 4.4 | | 37 |
| 1 | 1.5 | 4.8 | 35 | <1 |
| 1 | 2.8 | 6.6 | 36 | <1 |
| 2 | 2.6 | 7.2 | 34 | 37 |
| 2 | 5.2 | 4.4 | 45 | 20 |
| 3 | 2.4 | 5.0 | 46 | 39 |
| 3 | 5.0 | 6.6 | 56 | 24 |
| 4 | 2.6 | 5.8 | 75 | 10 |
| 4 | 4.8 | 7.6 | 64 | <2 |
| 7 | 2.6 | 4.6 | 32 | 37 |
| 7 | 5.2 | 5.3 | 39 | 33 |
| 7 | 6.4 | 4.4 | 46 | 34 |
| 8 | 2.5 | 5.7 | 35 | 37 |
| 8 | 5.3 | 4.6 | 33 | 15 |
| 9 | 3.5 | 5.7 | 34 | 41 |
| 9 | 4.5 | 5.9 | 43 | 6 |
| 12 | 2.2 | 5.4 | 43 | 36 |
| 12 | 4.4 | 6.2 | 54 | 27 |

*Reference: the tested substrate fabric with no additives- Suominen Hydraspun 8401 at 55 gr/sqm
**Water harness was between 95 and 100 ppm.

Example 5

Tissues Preparation with ISP 2

Materials
1. ISP 2 (15-17% by weight solids solution) prepared in Example 2.
2. Dispersible non-woven fabric, 55 gr/sqm (=Control).
3. Wetting composition comprising: at least 2% sodium chloride, and optionally preservative, solubilizing agents, skin conditioning agents, perfume, etc.

Sample Preparation

Samples were prepared according to the following procedure:
1. Cutting the control fabric into sample size of 14×15 cm (surface 210 cm$^2$);
2. Weighting the initial sample (IS);
3. Placing the sample in a petri dish, and covering it with 7 g of solution containing ISP 2 per 100 cm$^2$;
4. Waiting for 5 min (impregnation);
5. Drying the sample at a temperature of about 100° C. to about 105° C.;
6. Weighting the dry sample (DS);
7. Determining the add-on (A) as the ratio: (A=) DS weight/ IS weight;
8. Cutting the dry samples to:
   a) size 5×14 cm for tensile measurements,
   b) size 10×10 cm for testing of the flushable properties;
9. Wetting the samples with the wetting composition at a ratio of 1:2.5 tissue to wetting composition; and
10. Placing the wet samples (WS) in a flexible film (PE/PET laminate) envelope for a predetermined time.

Samples at dry add-on of 1.5%-7.6% were obtained.

Example 6

Testing ISP 2 Containing Wet Samples (WS)

1. Measurement of Cross-Direction (CD) Force at Peak
   The peak cross-direction force was measured according to the following procedure:

Determining the Tensile force of WS at peak F by using Hounsfield machine (or any other acceptable instrument); and Measuring the cross direction (CD), which is the weaker and critical strength direction.

2. Disintegration

Procedure (Lab test method 1):

Placing the WS's in a glass beaker;

Adding tap hard water and a magnetic stirrer;

Stirring the sample for 20 hours at 150 RPM;

Placing the sample on a special stainless steel filter with 3 mm holes and washing same under a stream of tap water;

Collecting the residue (RS) from the filter, and drying it at 105° C. until it reaches constant weight;

Weighing the dried sample.

The result is the ratio of the dry residue's weight to the initial dry sample's weight: (D=) RS weight/IS weight 3. Results Wet Samples (WS) Disintegration Testing The strength of the above impregnated samples 72 hours after impregnation (N/5 cm) is shown in Table 4:

TABLE 4

| | % dry add-on of ISP 2 | | |
|---|---|---|---|
| Control fabric | 7.4 | 3.7 | 1.7 |
| | 3.27 | 13.77 | 10.17 | 6.91 |
| | 4.57 | 13.60 | 9.23 | 6.13 |
| | 2.87 | 12.91 | 12.27 | 6.23 |
| | 2.97 | 13.52 | 10.03 | 6.73 |
| | 3.53 | 12.63 | 9.41 | 6.48 |
| Mean | 3.42 | 13.26 | 10.21 | 6.51 |

Disintegration After 20 Hours in Tap Water

TABLE 5

A. Non-impregnated control fabric

| | Sample | | | | | |
|---|---|---|---|---|---|---|
| | 1 | 2 | 3 | 4 | 5 | Mean |
| IS-Start weight, g | 0.570 | 0.569 | 0.556 | 0.577 | 0.560 | 0.566 |
| DS-Finish weight, g | 0.268 | 0.271 | 0.249 | 0.283 | 0.257 | 0.266 |
| Amount dispersed, g | 0.302 | 0.298 | 0.307 | 0.294 | 0.303 | 0.301 |
| % dispersed | 53% | 52% | 55% | 51% | 54% | 53% |

TABLE 6

B. Control fabric + 7.4% add-on ISP 2

| | Sample | | | | | |
|---|---|---|---|---|---|---|
| | 1 | 2 | 3 | 4 | 5 | Mean |
| IS-Start weight, g | 1.232 | 1.261 | 1.252 | 1.241 | 1.257 | 1.249 |
| DS-Finish weight, g | 1.207 | 1.241 | 1.223 | 1.220 | 1.229 | 1.224 |
| Amount dispersed, g | 0.025 | 0.020 | 0.029 | 0.021 | 0.028 | 0.025 |
| % dispersed | 2.0% | 1.6% | 2.3% | 1.7% | 2.2% | 2.0% |

TABLE 7

C. Control fabric + 3.7% add-on ISP 2

| | Sample | | | | | |
|---|---|---|---|---|---|---|
| | 1 | 2 | 3 | 4 | 5 | Mean |
| IS-Start weight, g | 1.205 | 1.21 | 1.204 | 1.185 | 1.197 | 1.200 |
| DS-Finish weight, g | 0.990 | 0.965 | 0.969 | 0.963 | 0.940 | 0.965 |
| Amount dispersed, g | 0.215 | 0.245 | 0.235 | 0.222 | 0.257 | 0.235 |
| % dispersed | 18% | 20% | 20% | 19% | 21% | 20% |

TABLE 8

D. Control fabric + 1.7% add-on ISP 2

| | Sample | | | | | |
|---|---|---|---|---|---|---|
| | 1 | 2 | 3 | 4 | 5 | Mean |
| IS-Start weight, g | 1.217 | 1.213 | 1.185 | 1.233 | 1.196 | 1.209 |
| DS-Finish weight, g | 0.730 | 0.720 | 0.664 | 0.750 | 0.761 | 0.725 |
| Amount dispersed, g | 0.487 | 0.493 | 0.521 | 0.483 | 0.435 | 0.484 |
| % dispersed | 40% | 41% | 44% | 39% | 36% | 40% |

Example 7

Dispersability Shake Flask Test

In order to evaluate the physical dispersability of the wet wipes of the invention when disposed of in the home drainage system, as well as to evaluate their degradation level in tap water or waste water, the Shake-Flask Die-Away Test methods (e.g. ASTM and U.S EPA) were performed. The only difference was that instead of using river water and testing for chemicals, we used tap water or waste water to test wet wipes. The test was used to simulate the physical conditions that leads to the degradation of the wet wipes when passing through the sewer system.

1. Measuring the sample prior to the test;
2. Placing the sample in vessel containing water;
3. Tilting the vessel by using a shaker for a predetermined period of time;
4. Removing the sample and analyzing its degradation level, e.g.:
   a) visual look (holes, tears, etc.),
   b) physical strength,
   c) weight of the sample (before vs. after treatment).

Example 8

Comparison of the Lion Polymer with ISP 2 of the Invention

Samples were prepared as described above, and were impregnated for at least 24 hours with a wetting solution comprising either the lion polymer or ISP 2. After impregnation, the samples were analyzed. The results are summarized in Table 9 below:

TABLE 9

| | Add-On % | CD Force at break N/5 cm | Disintegration % at 100 ppm $Ca^{++}$ |
|---|---|---|---|
| Lion polymer | 0 | 4.4 | 37 |
| | 1.5 | 4.8 | <1 |
| | 2.8 | 6.6 | <1 |

TABLE 9-continued

|  | Add-On % | CD Force at break N/5 cm | Disintegration % at 100 ppm Ca$^{++}$ |
|---|---|---|---|
| ISP 2 | 0 | 3.43 | 37 |
|  | 1.9 | 5.67 | 34 |
|  | 3.5 | 7.86 | 7 |

All methods described herein can be performed in any suitable order unless otherwise indicated herein or otherwise clearly contradicted by context. The use of any and all examples, or exemplary language (e.g., "such as") provided herein, is intended merely to better illustrate the invention and does not pose a limitation on the scope of the invention unless otherwise claimed. No language in the specification should be construed as indicating any non-claimed element as essential to the practice of the invention.

While the present invention has been described above in connection with the certain illustrative embodiments, it is to be understood that other similar embodiments may be used or modifications and additions may be made to the described embodiments for performing the same function of the present invention without deviating therefrom. Furthermore, all embodiments disclosed are not necessarily in the alternative, as various embodiments of the invention may be combined to provide the desired characteristics. Variations can be made by one having ordinary skill in the art without departing from the spirit and scope of the invention. Therefore, the present invention should not be limited to any single illustrative embodiment, but rather construed in breadth and scope in accordance with the recitation of the attached claims.

The invention claimed is:

1. An ion-sensitive polymer formed from the following monomers: acrylic acid, butyl acrylate, 2-ethylhexyl acrylate, and an allyl derivative of polyethylene-glycol (PEG), the polymer comprising from about 35 to about 55 weight % acrylic acid; from about 25 to about 40 weight % butyl acrylate; from about 10 to about 25 weight % 2-ethylhexyl acrylate; and from about 5 to about 20 weight % allyl derivative of PEG.

2. The ion-sensitive polymer of claim 1, which is insoluble in a salt solution containing 2-5 weight % monovalent or multivalent ions, and which is soluble in tap water containing 10-300 ppm calcium ions.

3. The ion-sensitive polymer of claim 1, wherein said allyl derivative PEG is selected from the group consisting of diethylene glycol allyl, triethylene glycol allyl, and tetraethylene glycol allyl, or any combination thereof.

4. A binder composition for binding fibrous material into an integral web, comprising the ion-sensitive polymer of claim 1.

5. The binder composition of claim 4, wherein the content of ion-sensitive polymer is from about 5% to about 50% by weight.

6. A disposable and flushable, water-decomposable article comprising a fibrous web substrate and
   (a) an ion-sensitive polymer formed from the following monomers: acrylic acid, butyl acrylate, 2-ethylhexyl acrylate, and an allyl derivative of polyethylene-glycol (PEG), the polymer comprising from about 35 to about 55 weight % acrylic acid; from about 25 to about 40 weight % butyl acrylate; from about 10 to about 25 weight % 2-ethylhexyl acrylate; and from about 5 to about 20 weight % allyl derivative of PEG, or
   (b) a binder composition for binding fibrous material into an integral web, comprising the ion-sensitive polymer.

7. The disposable and flushable, water-decomposable article of claim 6, selected from the group consisting of wet wipes, infant care products, child care products, adult care products, feminine care products, medical care products, surgical products, packaging materials, and household wipes.

8. The disposable and flushable, water-decomposable article of claim 6, wherein the substrate is a nonwoven fabric.

9. The disposable and flushable, water-decomposable article of claim 6, wherein the content of the binder in the fabric is no more than 10% by weight relative to the weight of the fabric.

10. The disposable and flushable, water-decomposable article of claim 9, wherein the content of the binder in the fabric is no more than 6% by weight relative to the weight of the fabric.

11. The disposable and flushable, water-decomposable article of claim 9, wherein the content of the binder in the fabric is no more than 3% by weight relative to the weight of the fabric.

12. A method of producing the disposable and flushable, water-decomposable article of claim 8, comprising the steps of:
   applying the binder composition of claim 4 onto the fabric;
   drying the fabric;
   cutting the fabric into a desired size and shape;
   impregnating it with the wet wipe lotion; and
   packing the fabric in a liquid-proof package.

13. The method of producing the disposable and flushable, water-decomposable article according to claim 12, wherein the binder composition of claim 4 is applied directly onto the fibers of said substrate, during or after the formation of the fabric.

* * * * *